(12) United States Patent
Cully et al.

(10) Patent No.: US 9,539,360 B2
(45) Date of Patent: Jan. 10, 2017

(54) PUNCTURABLE AND RESEALABLE GRAFT

(71) Applicant: W. L. Gore & Associates, Inc, Newark, DE (US)

(72) Inventors: Edward H. Cully, Flagstaff, AZ (US); Jeffrey B. Duncan, Flagstaff, AZ (US); Paul D. Gassler, Lincoln University, PA (US)

(73) Assignee: W. L. Gore & Associaes, Inc., Newark, DE (US)

( * ) Notice: Subject to any disclaimer, the term of this patent is extended or adjusted under 35 U.S.C. 154(b) by 942 days.

(21) Appl. No.: 13/644,160

(22) Filed: Oct. 3, 2012

(65) Prior Publication Data

US 2013/0090723 A1 Apr. 11, 2013

Related U.S. Application Data

(60) Provisional application No. 61/545,044, filed on Oct. 7, 2011.

(51) Int. Cl.
| | |
|---|---|
| *A61F 2/07* | (2013.01) |
| *A61L 27/16* | (2006.01) |
| *A61L 27/34* | (2006.01) |
| *A61L 27/50* | (2006.01) |

(52) U.S. Cl.
CPC ............... *A61L 27/16* (2013.01); *A61L 27/34* (2013.01); *A61L 27/50* (2013.01); *A61L 27/507* (2013.01); *A61L 2420/02* (2013.01); *A61L 2420/08* (2013.01); *Y10T 29/49826* (2015.01)

(58) Field of Classification Search
None
See application file for complete search history.

(56) References Cited

U.S. PATENT DOCUMENTS

| 8,163,002 B2 | 4/2012 | Weinberg |
| 2007/0123968 A1 | 5/2007 | Weinberg |

(Continued)

FOREIGN PATENT DOCUMENTS

| JP | 2008511418 | 4/2008 |
| JP | 2011512201 | 4/2011 |

(Continued)

OTHER PUBLICATIONS

International Search Report and Written Opinion for PCT/US2012/058597 mailed Jan. 2, 2013, corresponding to U.S. Appl. No. 13/644,160.

*Primary Examiner* — Yashita Sharma
*Assistant Examiner* — Wade P Schutte

(57) ABSTRACT

Implantable grafts, particularly for arteriovenous access that may be punctured by an object such as a needle and, following removal of the object, will reseal the resulting hole to the extent of reducing fluid leakage through the graft at the puncture site to an amount less than would be typical for a conventional graft. More particularly, the grafts comprise three layers; an inner layer of implantable graft material such as ePTFE, a middle layer of self sealing elastomeric material such as silicone, and an outer layer of implantable graft material such as ePTFE. Following manufacture, the tubular form of the three-layer graft is everted to put substantially the entire wall thickness of the elastomeric material layer under circumferential compression.

16 Claims, 1 Drawing Sheet

(56) References Cited

U.S. PATENT DOCUMENTS

| | | | |
|---|---|---|---|
| 2007/0167901 A1* | 7/2007 | Herrig | A61M 39/0208 |
| | | | 604/6.16 |
| 2007/0213838 A1 | 9/2007 | Hengelmolen | |
| 2009/0227026 A1* | 9/2009 | Rapoport | A61F 2/06 |
| | | | 435/402 |
| 2011/0112618 A1 | 5/2011 | Cleek et al. | |
| 2011/0268781 A1* | 11/2011 | Cleek | A61L 29/085 |
| | | | 424/422 |

FOREIGN PATENT DOCUMENTS

| | | |
|---|---|---|
| WO | 2006/058322 | 6/2006 |
| WO | 2007/061787 | 5/2007 |

\* cited by examiner

PUNCTURABLE AND RESEALABLE GRAFT

CROSS REFERENCE TO RELATED APPLICATIONS

This application claims priority to U.S. Provisional Application Ser. No. 61/545,044 filed Oct. 7, 2011.

FIELD OF THE INVENTION

The present invention relates to the field of implantable grafts, particularly grafts for arteriovenous access, that may be punctured by an object such as a needle and, following removal of the object, will reseal the resulting hole to the extent of reducing fluid leakage through the graft at the puncture site to an amount less than would be typical for a graft.

BACKGROUND OF THE INVENTION

Various grafts have been described in the literature that have attempted to offer solutions to the problem of reducing leakage of fluids from puncture sites following removal of the puncturing object. Typical graft materials for these grafts, which are most typically grafts intended for arteriovenous access wherein the graft may be pierced repeatedly, at intervals, by dialysis needles, are polyethylene terephthalate (PET) and expanded polytetrafluoroethylene (ePTFE). These grafts are typically tubular grafts, although planar sheet grafts, often for use in patching a portion of the surface of a tube, are also known.

A construction that has been described previously in various forms for reduced leakage involves the use of laminates of the above materials with a layer of a self-sealing material such as an implantable elastomeric material. These elastomeric materials are typically silicone, polyurethane or fluoroelastomers. The use of one layer of graft material joined to one layer of elastomeric material has been described, although the most frequently described laminates involve a layer of the elastomeric material that is covered on both surfaces (e.g., inner and outer surfaces) by a layer of the graft material. The layers of graft material may be the same or may be different materials on the two surfaces; the graft materials may also differ in thickness, bulk density, porosity, orientation or other attributes even if they are essentially of the same chemical makeup.

A particular variation of these laminates, particularly for tubular constructions, involves the use of a tubular elastomeric material component that has been everted (i.e., turned inside out) prior to laminating this tube to one or more layers of graft material). The everted tube of elastomeric material is under circumferential compression at its luminal surface while the abluminal surface is under circumferential tension.

SUMMARY OF THE INVENTION

Figures 1A, 1B:
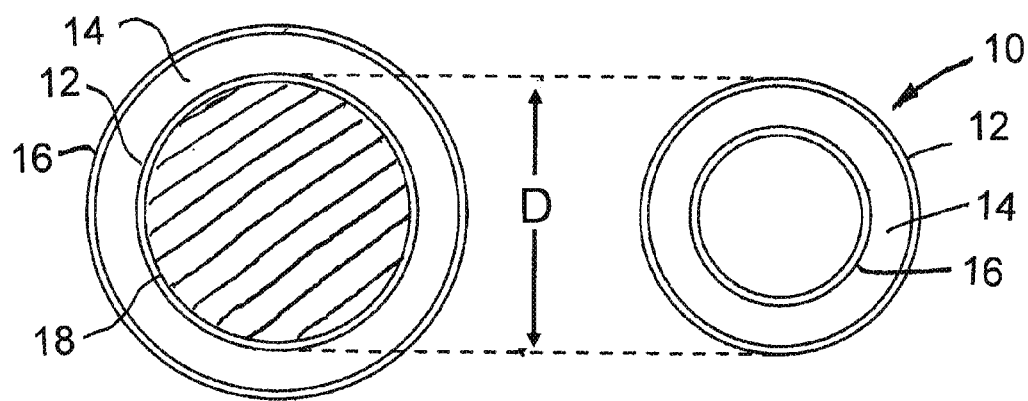
FIG. 1A describes a transverse cross section of one embodiment of the graft described herein as manufactured on a cylindrical mandrel.
FIG. 1B shows a transverse cross section of the graft shown in FIG. 1A after it has been removed from the mandrel and everted by turning the tube of FIG. 1A inside out.

Implantable grafts are described, particularly grafts for arteriovenous access that may be punctured by an object such as a needle and, following removal of the object, will reseal the resulting hole to the extent of reducing fluid leakage through the graft at the puncture site to an amount less than would be typical for a graft. More particularly, the grafts comprise three layers; an inner layer of implantable graft material such as ePTFE, a middle layer of self sealing elastomeric material such as silicone, and an outer layer of implantable graft material such as ePTFE. Following manufacture, as will be further described, the tubular form of the three-layer graft is everted to put substantially the entire wall thickness of the elastomeric material layer under circumferential compression.

The outer layer of graft material (the inner layer prior to everting the tube) is a high tensile strength material with the high strength direction oriented circumferentially about the tubular graft. The strength of the graft material may be appreciably less in the longitudinal direction of the tubular graft. One such material is ePTFE film that has been cut into a tape of greater length than width and with the high strength direction parallel to the length of the tape. This tape is used to create a helical winding that constitutes an outer surface of the completed (post-eversion) tubular graft.

The graft may be made by helically wrapping the ePTFE tape about the surface of a mandrel. The films from which the tapes are cut are generally described by U.S. Pat. No. 3,953,566, incorporated by reference herein. Preferred films have high strength in one direction which is the direction of fibrillar orientation for uniaxial films, with the fibrils oriented to be substantially parallel to the length of ePTFE tapes cut from such films. The helical wrapping may be in a single direction along the length of the chosen mandrel, with the result that the strength direction of the wrapping is substantially in the circumferential direction as opposed to the longitudinal direction. In another embodiment the helical wrapping may be performed in both in both directions along the length. In another embodiment, multiple wrapping passes along the mandrel length may be made if desired.

Following completion of the helically wrapped film layer, the layer of elastomeric material is provided. Silicone of selected durometer may be used in one embodiment; in other embodiments polyurethanes may be used. Still another embodiment provides a fluoroelastomer for this layer such as a copolymer of tetrafluoroethylene and a polyalkylvinylether (TFE/PAVE); one such is a copolymer of TFE and polymethylvinylether (TFE/PMVE). These materials are taught by U.S. Pat. No. 7,049,380 and US 2006/00198866, incorporated by reference herein. The elastomeric material may be applied over helically-wrapped films by various methods, including the use of pre-formed tubes of the elastomeric material or alternatively the material may be applied in an uncured form over the helically wrapped film, such as by dip coating or spray coating. Some of these methods are taught by U.S. Pat. No. 8,029,563, also incorporated by reference herein. The elastomeric material may be cured or partially cured following application.

Additionally, combinations of the above-mentioned elastomers are also contemplated. For example, a layer of fluoroelastomer (e.g., TFE/PMVE copolymer) may be applied over a vascular graft substrate tube and allowed to dry, followed by an additional layer of silicone. Likewise, the inner/outer relationship of the two different elastomers may be reversed. Also, combinations of the same type of elastomers having different forms may be applied, such as an inner layer of silicone may be applied first over the vascular graft substrate tube followed by a second layer of silicone that is an uncured layer. In this fashion, one layer of cross-linked elastomer provides the necessary force to compress and seal a needle puncture site while the second outer layer of elastomer (which may also be a partially cured layer of the same type of elastomer) that, in use, may be expected to flow and "heal" the puncture site following needle removal. It is apparent that the relationships of inner and outer layers as described during construction will be reversed following eversion of the constructed tubular form (as will be described below) to result in a finished tubular graft available for use (following the necessary step of sterilization by suitable means) as a vascular graft intended for dialysis applications.

Finally, an additional layer of graft material (e.g., PET or ePTFE) is applied over the elastomeric material. In one embodiment this is ePTFE and more particularly may be a longitudinally extruded and expanded tube of ePTFE. In one embodiment this tube has a wall thickness of about 0.1 mm and a mean fibril length of about 25-35 microns. It is apparent that these dimensions may be varied as desired. Alternatively, this layer may be made of helically wrapped ePTFE film. This graft layer of graft material may be joined to the underlying layer of elastomeric material by an adhesive such as an implantable silicone medical adhesive, or by curing the underlying elastomeric material after the outer graft material is provided.

It is further apparent that the graft layers may also include additional elastomeric materials so long as the intermediate elastomeric material layer described above is included.

Following completion of the above-described three layers including the intermediate layer of elastomeric material with both sides covered with graft material, the resulting tubular graft material is removed from the mandrel. In one embodiment, this removal is accomplished by everting the tubing back over itself and removing it from the mandrel during the process of eversion. Alternatively, the tubular construct may be everted after removal from the mandrel.

The layer of helically wrapped graft material with the predominant strength direction oriented substantially circumferentially has a diameter that is substantially unchanged by the step of everting the tube. The materials that were provided over the helically wrapped layer while still on the manufacturing mandrel become circumferentially compressed during eversion of the tube wherein the elastomeric material layer in particular is reduced in diameter and remains in a state of circumferential compression that aids significantly in reducing puncture site leakage of the resulting graft. This is anticipated to be of particular use for vascular grafts intended for dialysis, possible in-situ fenestration for side branch endoprosthesis placement, and is similarly useful for grafts that have been punctured by suture needles.

An indication of the elastomeric material layer being in a state of circumferential compression through substantially its entire wall thickness may be seen by taking a length of the everted tube made as described above and cutting it through the wall in a longitudinal direction, parallel to the longitudinal axis of the tube. After being cut through, the resulting sheet will curl in a direction opposite to the curvature of the original everted tube, i.e., the outer surface of the curled sheet will have previously been the luminal surface of the everted tube.

Additionally, a completed implantable vascular graft made generally as described above (e.g., including the step of eversion following removal from the mandrel on which it was constructed) has a tubular structure with a first outside diameter wherein, when that tubular structure is everted, has a second outside diameter that is larger than the first outside diameter. This eversion to the second larger outside diameter, is in effect a second eversion back to its condition as manufactured on the mandrel prior to: removal from the mandrel and the first eversion during manufacture. The second outside diameter is typically larger than the first outside diameter by an amount that is equal to at least the wall thickness of the tubular structure.

Wall thickness is preferably measured by fitting the tubular structure over a mandrel that is a snug fit to the inside diameter of the tubular structure, the snug fit requiring a small force to fit the tube over the mandrel surface. The use of substantial force to fit the tube to the mandrel may result in an undesired increase of the outside diameter of the tube. When fitted over a mandrel of appropriate diameter, the outside diameter of the tube may be measured with a suitable laser micrometer. The wall thickness is the indicated outside diameter of the tube minus the mandrel diameter, divided by two. At least three measurements should be made at different locations along the length of the tube, the wall thickness being the average of the three measurements.

The graft may also be provided in planar form. In one embodiment this may be accomplished simply by cutting a tube made as described above along its length.

Other methods for applying compressive stresses to the elastomer are also envisioned. One method involves the fabrication of one component as a composite tube having an ePTFE liner and cured or semi-cured coating of silicone, a second component being an ePTFE tube having significant radial strength and fabricated at a slightly smaller diameter than the first component, and then placing the first component into the second component. The components may be slipped together where interference fit holds them in place or, they may be fitted together and adhered in place by using a thin coating of silicone adhesive prior to fitting the two tubes together. In either case, the ePTFE tube of component two will hold the composite tube of component one at a smaller size than originally fabricate, resulting in residual compressive stresses throughout the thickness of the elastomeric layer. Component two may be provided with a stent component if desired, thereby creating a stent-graft Utilizing residual compressive stresses within the elastomer, the puncture tolerance of the present invention is increased dramatically. This increase in tolerance allows for reduced graft wall thickness in comparison to prior devices while still providing effective leak resistance. This reduction in thickness has provided for the fabrication of a true endoluminal graft or stent-graft that may be diametrically compacted to an appropriate insertion profile and mounted upon or within a delivery system for subsequent deployment at a desired site to its larger diameter.

The stent structure may be provided to at least a portion of the length of the tubular graft material. The stent structure may be self-expanding or may be balloon expandable. The balloon expandable stents may be machined from a plastically deformable metal such as any of various implantable stainless steels. Self-expanding stents may be made of nitinol and more particularly made of nitinol wire. One such embodiment uses nitinol wire that has been helically wound into a generally tubular form; a variation of this embodiment uses wire that has been bent into a serpentine pattern with alternating apices directed in opposing directions, and then this serpentine wire is helically wound into the generally tubular shape; see, for example, U.S. Pat. No. 6,551,350, incorporated by reference herein. The stent structure may be provided on the outer surface of the above-described tubular graft in one embodiment. In another embodiment the stent may be provided on the inner surface of the graft and in another embodiment the stent structure may be incorporated into the wall thickness of the graft. In another embodiment the stent structure may be provided at one or both ends of the graft as generally taught by US 2007/0198077 and US 2007/0076587.

DETAILED DESCRIPTION OF THE DRAWINGS

FIG. 1A describes a transverse cross section of one embodiment of the graft described herein as manufactured on a cylindrical mandrel while FIG. 1B shows the same graft after it has been removed from the mandrel and everted by turning the tube of FIG. 1A inside out. As shown by FIG. 1A, mandrel 18 is provided with a covering 12 of a graft material having a high circumferential strength, such as a helical wrapping of a thin ePTFE tape having a uniaxial microstructure with the strength direction of the tape parallel to the length of the tape whereby circumferential strength is provided when the mandrel is helically wrapped with such a tape. Next, one or more layers of an elastomeric material 14 are provided over the helical wrapping of tape 12, after which another covering 16 of graft material is provided over the elastomeric material 14. In one embodiment this covering 16 is porous ePTFE and may be a longitudinally extruded and expanded ePTFE tube or alternatively may be provided as a helical wrapping of ePTFE.

FIG. 1B is a transverse cross section of the tube of FIG. 1A following removal of the mandrel 18 and following eversion of the composite tube, resulting in implantable tubular vascular graft 10. It is noteworthy that the outside diameter "D" of graft 10 is substantially the same as the outside diameter of covering 12 as laid up on mandrel 18 shown in FIG. 1A prior to eversion. Elastomeric material layer 14 of implantable tubular vascular graft is now circumferentially compressed and constrained by cover 12 following eversion as shown in FIG. 1B. It is noteworthy that substantially the entire thickness of the elastomeric layer is under circumferential compression which in combination with the material properties of the elastomeric material chosen provides graft 10 with its self-sealing capability. The outer portion of the wall thickness of the layer of elastomeric material is under the least amount of circumferential compression (little or no circumferential compression) and the inner portion of the wall thickness of the layer of elastomeric material is under the greatest amount of circumferential compression. It is possible that the wall thickness of this layer of elastomeric material may slightly increase following eversion. Covering 16 is also circumferentially compressed, now providing the luminal surface of graft 10. The porous material of layer 16, such as an ePTFE tubular structure, easily accommodates this compression without appreciable deformation at the luminal surface.

Examples

An ePTFE tape of about 2.5 mm width and about 0.0025 mm thickness was obtained, the tape having a substantially uniaxial fibrillar microstructure with a matrix tensile strength of about 26000 psi (180 MPa) in the high strength direction (along the length) of the tape. This material had a bulk density of about 0.6 g/cc, in comparison to the density of non-porous PTFE of about 2.2 g/cc. A stainless steel mandrel of about 8 mm diameter was obtained and provided with a tubular covering of a longitudinally extruded and expanded ePTFE (thickness about 0.25 mm). A helical wrapping of the obtained tape was applied by wrapping the tape over the covered mandrel in one direction only with a resulting thickness of 5 layers of the tape along the length of the resulting tube. The assembly was placed into a convection oven set at 370° C. for 10 minutes, after which time it was removed from the oven and allowed to cool. The mandrel was removed and replaced with another of the same size that had been provided with a surface covering of a release material (e.g., Kapton). The ePTFE tube was then provided with a coating of Nusil MED-1137 Silicone (Nusil Technology, Carpenteria Calif. 93013) which was smoothed manually. Before the silicone cured to the point of hardening it was then helically wrapped in three passes (in alternating directions) with another 5 layers of the same film per pass (total 15 layers). This was followed by another application of silicone and with another 5 layers of film helically wrapped in one direction. The assembly was placed into an oven set at 65° C. for 20 or more hours to cure the silicone. A container of de-ionized water was placed into the oven during this time to assist in the curing process. After completion of this time the assembly was removed from the oven and the mandrel was removed from the tubular construct, after which the tubular construct was everted to create the tubular graft.

The resulting graft had a total wall thickness of about 0.38 mm. It was tested by pressurizing with room temperature water at 2.5 psi (17.2 KPa), and then inserting a new 16 gauge dialysis needle through the wall of the graft at an angle of about 45 degrees, with the beveled surface of the needle facing up. When the needle was removed from the pressurized graft there was a small stream of water from the puncture site that lasted about two seconds, after which a droplet of water formed momentarily at the puncture site. Leakage of the pressurized graft then stopped entirely.

Another graft was made with the same process, using a slightly lesser amount of silicone with a resulting wall thickness of about 0.33 mm. This graft, after fitting over a stainless steel mandrel, was provided with a helically wrapped covering of a TFE/PMVE fluoroelastomer tape (material made according to U.S. Pat. No. 7,049,380) of 2.5 cm width, applied at a pitch that resulted in a 3 layer thick application of this tape. Another 5 layers of the above-described ePTFE tape was wrapped around the outer surface to secure the fluoroelastomer and to cause it to flow to create a uniform thin covering. This construct was placed into a convection oven set at 220° C. for 15 minutes, then removed and allowed to cool, after which the mandrel was removed. The resulting graft, after eversion, had a wall thickness of about 0.41 mm. When pressure tested as described above, when the dialysis needle was removed a water droplet formed momentarily at the puncture site, immediately after which all leakage stopped.

The outer surface of a length of graft made as described above using only silicone as the elastomeric material was fitted with a nitinol serpentine wire stent (wire diameter about 0.2 mm). The stent was adhered to the outer surface of the stent using the TFE/PMVE fluoroelastomer described above as a melt-bond adhesive. The stent was made generally as described for the stent-graft portion of the device described in U.S. Pat. No. 6,673,102, incorporated by reference herein. The resulting stent-graft was compacted to a diameter of about 13 French (about 4.3 mm) using a funnel-type compactor as described in U.S. Pat. No. 6,673,102. This demonstrates that such a stent-graft may be implanted and deployed endoluminally.

In addition to being directed to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

We claim:

1. A method of making an implantable tubular graft comprising:
   a). providing a cylindrical mandrel having a surface;
   b). providing the mandrel surface with a wrapping of a first graft material that has a high strength orientation in a direction that is substantially circumferential with respect to the surface of the mandrel;
   c). providing the wrapping of first graft material with a covering of an elastomeric material;
   d). providing the elastomeric material with a covering of a second graft material;
   e). removing the resulting tubular structure from the mandrel and everting the tubular structure such that substantially the entire thickness of the elastomeric layer is under circumferential compression from the first graft material following eversion of the implantable tubular vascular graft.

2. A method according to claim 1 wherein said first graft material is ePTFE.

3. A method according to claim 1 wherein said second graft material is ePTFE.

4. A method according to claim 3 wherein said first graft material is ePTFE.

5. A method according to claim 1 wherein said elastomeric material is silicone.

6. A method according to claim 1 wherein said elastomeric material is a fluoroelastomer.

7. A method according to claim 6 wherein said elastomeric material is a copolymer of tetrafluoroethylene and polyalkylvinylether.

8. A method according to claim 7 wherein said elastomeric material is a copolymer of tetrafluoroethylene and polymethylvinylether.

9. A method according to claim 1 wherein said elastomeric material is a polyurethane.

10. A method according to claim 1 wherein the elastomeric material comprises two layers of different elastomers.

11. A method according to claim 10 wherein one of the different elastomers is a silicone and another of the different elastomers is a fluoroelastomer.

12. A method according to claim 11 wherein, for the everted tubular structure, the two layers comprise an outer layer of fluoroelastomer and an inner layer of silicone.

13. A method according to claim 11 wherein, for the everted tubular structure, the two layers comprise an inner layer of fluoroelastomer and an outer layer of silicone.

14. A method according to claim 1 wherein the tubular structure has a larger outside diameter prior to eversion than it does following eversion.

15. A method according to claim 1 wherein the tubular structure has a first, larger outside diameter prior to eversion and a second, smaller outside diameter following eversion.

16. A method according to claim 1 wherein the tubular structure has a first, larger outside diameter and a first larger inside diameter prior to eversion, and a second, smaller outside diameter and a second smaller inside diameter following eversion, wherein the difference between the first outside diameter and the second outside diameter is greater than the difference between the first inside diameter and the second outside diameter.

* * * * *